US011820780B2

(12) United States Patent
Pouyet et al.

(10) Patent No.: US 11,820,780 B2
(45) Date of Patent: *Nov. 21, 2023

(54) GOLD-CATALYSED PROCESS FOR MANUFACTURING CHROMENES INTENDED FOR THE PREPARATION OF THERMOSETTING RESINS

(71) Applicants: ARIANEGROUP SAS, Paris (FR); CENTRE NATIONAL DE LA RECHERCHE SCIENTIFIQUE, Paris (FR); UNIVERSITE DE REIMS CHAMPAGNE-ARDENNE, Reims (FR)

(72) Inventors: Robin Pouyet, Le Haillan (FR); Xavier Coqueret, Reims (FR); Brigitte Defoort, Le Haillan (FR); Bastien Rivieres, Le Segur (FR)

(73) Assignees: ARIANEGROUP SAS, Paris (FR); CENTRE NATIONAL DE LA RECHERCHE SCIENTIFIQUE, Paris (FR); UNIVERSITE DE REIMS CHAMPAGNE-ARDENNE, Reims (FR)

( * ) Notice: Subject to any disclaimer, the term of this patent is extended or adjusted under 35 U.S.C. 154(b) by 741 days.

This patent is subject to a terminal disclaimer.

(21) Appl. No.: 16/936,966

(22) Filed: Jul. 23, 2020

(65) Prior Publication Data
US 2021/0024534 A1    Jan. 28, 2021

(30) Foreign Application Priority Data
Jul. 23, 2019 (FR) ..................... 1908325

(51) Int. Cl.
*C07D 493/04* (2006.01)
*B01J 31/24* (2006.01)
*C08G 61/12* (2006.01)

(52) U.S. Cl.
CPC ............ *C07D 493/04* (2013.01); *B01J 31/24* (2013.01); *C08G 61/122* (2013.01); *C08G 2261/11* (2013.01); *C08G 2261/3242* (2013.01)

(58) Field of Classification Search
None
See application file for complete search history.

(56) References Cited

U.S. PATENT DOCUMENTS

| 5,155,196 A | 10/1992 | Kolb et al. |
| 11,591,343 B2 * | 2/2023 | Pouyet ............... C07D 413/04 |
| 2003/0065187 A1 | 4/2003 | Buchwald et al. |
| 2012/0309927 A1 | 12/2012 | Kim et al. |
| 2019/0040178 A1 * | 2/2019 | Rivieres ............... C08L 61/14 |

FOREIGN PATENT DOCUMENTS

| EP | 0 350 747 A2 | 1/1990 | |
| EP | 2842951 A1 * | 3/2015 | ........... C07D 311/70 |
| WO | WO 01/10861 A2 | 2/2001 | |
| WO | WO 2017/129661 A1 | 8/2017 | |

OTHER PUBLICATIONS

Sanglar, C., "Prepolymeres a Terminaisons Propargylique Et Chromene. Syntheses, Etudes Physicochimiques, Mecanismes Et Centique D_E Polymerisation a L'Etat Fondu." Doctoral Theses from L'Universite de Pau et des Pays de L'Adour, Centre Universitaire de Recherche Scientifique, Mention: Physicochimie des Polymeres, Nov. 13, 1995, 132 pages, (with translation of relevant portions).

Trahanovsky, W. S., et al., "Organic Oxalates. II. Formation of Bibenzyls by Pyrolysis of Benzyl Oxalates," Journal of the American Chemical Society, 90(11), (1968), pp. 2839-2842.

Search Report as issued in French Patent Application No. 1908325, dated Jun. 4, 2020.

Menon, R. S., et al., "The AU(I)-catalyzed Intramolecular hydroarylation of Terminal Alkynes Under Mild Conditions: Application to the Synthesis of 2H-Chromenes, Coumarins, Benzofurans, and Dihydroquinolines," J. Org. Chem., vol. 74, (2009), XP55082760, pp. 8901-8903.

Arcadi, A., et al., "Gold versus silver 1-7 catalyzed intramolecular hydroarylation reactions of [(3-arylprop-2-ynyl)oxy]benzene derivatives," Organic & Biomolecular Chemistry, vol. 10, No. 48, Jan. 2012, XP55700971, pp. 9700-9708.

Fang, W., et al., "Gold(I) catalyzed intramolecular hydroarylation and the subsequent ring enlargement of methylenecyclopropanes to cyclobutenes," RSC Advances, vol. 6, No. 46, Jan. 2016, XP55701069, pp. 40474-40479.

Christoudoulou, M. S., et al., "Divergent Palladium- and Platinum-Catalyzed Intramolecular Hydroamination/Hydroarylation of O-Propargyl-2-aminophenols," European Journal of Organic Chemistry, vol. 44, Jul. 2018, XP055693802, pp. 6176-6184, Retrieved from the Internet: URL:https://chemistry-europe.onlinelibrary.wiley.com/doi/full/10.1002/ejoc.201801103 [Retrieved on May 11, 2020].

Al-Sader et al., "On the Mechanism of Flash Vacuum Pyrolysis of Phenyl Propargyl Ether. Intramolecular Deuterium Kinetic Isotope Effect of Claisen Rearrangement," J. Org. Chem., vol. 43, No. 18, (1978), XP55701628, pp. 3626-3627.

(Continued)

*Primary Examiner* — Nicole M. Buie-Hatcher
(74) *Attorney, Agent, or Firm* — Pillsbury Winthrop Shaw Pittman LLP

(57) ABSTRACT

A process for manufacturing chromenes intended for the preparation of thermosetting resins, includes transforming an aromatic propargyl ether of general formula (I) into a chromene by homogeneous gold(I) catalysis with the catalyst (acetonitrile)[(2-biphenyl)di-tert-butylphosphine]gold (I) hexafluoroantimonate in an organic solvent under an inert or non-inert atmosphere. Moreover, a process for preparing a material made of thermoset resin, includes successively a) implementation of the above process; polymerization of the reaction product obtained in step a) so as to obtain the material made of thermoset resin; c) recovery of the material made of thermoset resin obtained in step b).

12 Claims, No Drawings

(56) References Cited

OTHER PUBLICATIONS

Parker, K. A., et al., "Electrocycling Ring Closure of the Enols of Vinyl Quinones. A 2H-Chromene Synthesis," Organic Letters, vol. 3, No. 24, (2001), XP55701593, pp. 3875-3878.

Liu, F., et al., "Blended Resins Based on New Propargyl-Functional Resin: Synthesis, Cure, and Thermal Properties," Journal of Applied Polymer Science, vol. 102, pp. 4207-4212, (2006).

Hashmi, et al., "Modern Gold Catalyzed Synthesis," Wiley-VCH Verlag & Co. KGaA, (2012), 408 pages.

Godschaix, J. P., et al., "Acetylene-Chromene Terminated Resins as High Temperature Thermosets," 22$^{nd}$ International SAMPE Technical Conference, Nov. 1990, pp. 163-174.

Reghunadhan, C. P., et al., "Bis propargyl ether resins: synthesis and structure-thermal property correlations," European Polymer Journal 35 (1999) 235-246.

Dirlikov, S. K., et al., "Propargyl-terminated Resins—A Hydrophobic Substitute for Epoxy Resins," High Performance Polymers, vol. 2, No. 1, (1990), pp. 67-77.

Prat, D., et al., "CHEM21 selection guide of classical- and less classical-solvents," Green Chem., (2016), 18, pp. 288-296.

Dirlikov, S. K., et al., "Propargyl Terminated Resins (PTR): Preperation and Thermostability," Polym. Mater., vol. 59, (1988), pp. 990-993.

Efe, C., e al., "Gold nanoparticles supported on TiO2 catalyse the cycloisomerisation/oxidative dimerisation of aryl propargyl ethers," Chem. Commun., (2011), vol. 47, pp. 803-805.

Echavarren, A. M., et al., "Chapter 1: Gold-Catalyzed Cyclizations of Alkynes With Alkenes and Arenes," Organic Reactions, vol. 92, (2017), 288 pages.

Dorel, R., et al., "Gold(I)-Catalyzed Activation of Alkynes for the Construction of Molecular Complexity," Chemical Reviews, (2015), vol. 115, pp. 9028-9072.

Rehman, H., et al., "Tandem Intramolecular Wittig and Claisen Rearrangement Reactions in the Thermolysis of 2-Methyl-2-Phenoxy-Propionyl-Cyanomethylenetriphenylphosphoranes: Synthesis of Substituted 2H-I-Benzopyrans and Benzofurans," Tetrahedron, vol. 43, No. 22, pp. 5335-5340, (1987).

Rehman, H., et al., "Synthesis of Benzofurans Via Tandem Intramolecular Witting and 3,3-Sigmatropic Reaction of Phenoxyacetyl-Cyanomethylenetriphenylphosphoranes," Synthetic Communications: An International Journal for Rapid Communication of Synthetic Orange Chemistry, (2006), 12 pages.

Ullenius, C., et al., "Formation of 2-Indanone and Benzocyclobutene from the Pyrolysis of Phenyl Ether," Department of Chemistry, University of Oregon, (1972), pp. 5911-5913.

Lazar, K. L., et al., "Optically detected magnetic resonance of α-deuterated 2-indanone," Journal of Luminescence, vol. 118, (2006), pp. 21-32.

Notice of Allowance as issued in U.S. Appl. No. 16/937,044, dated Jun. 28, 2023.

Wang, Y.-L., et al., "Cu-catalyzed intramolecular hydroarylation of alkynes," RSC Advances, 2014, 4, pp. 61706-61710, (Year: 2014).

* cited by examiner

GOLD-CATALYSED PROCESS FOR MANUFACTURING CHROMENES INTENDED FOR THE PREPARATION OF THERMOSETTING RESINS

CROSS REFERENCES TO RELATED APPLICATIONS

This application claims priority to French Patent Application No. 1908325, filed Jul. 23, 2019, the entire content of which is incorporated herein by reference in its entirety.

The present invention relates to the field of thermosetting resins and to materials obtained from these resins, and in particular to processes for manufacturing same. These resins are directed towards replacing phenolic resins in all the applications in which they are normally used, and notably "ablative" materials.

An ablative material is defined as being a material that can undergo ablation, i.e. a loss of substance by chemical decomposition, change of state or mechanical erosion under the effect of a flow of material or of radiation (Official Journal of the French Republic of 22 Sep. 2000). This is in particular the case for materials included in the construction of heat shields intended for the aerospace industry and the walls of propulsion engine exhaust nozzles. Typically, in this case, the outer layer of the ablative material which is in direct contact with the environment undergoes a chemical transformation under the effect of heat, and also a recession associated with this transformation. This outer layer thus radiates outwards and its chemical transformation consumes energy. These two effects contribute towards reduced heat transmission towards the inner layers of the material and thus to thermal insulation of the underlying structure. A good ablative material must be such that its chemical transformation under the effect of heat is endothermic, its thermal conductivity is low in a stationary and/or transitional regime and its chemical transformation is not accompanied by excessively rapid recession. In particular, to fulfill this last point, it is necessary for the chemical transformation of the ablative material to be accompanied by the formation of a crust based on carbon or silica originating from the pyrolysis of the resin.

This is in particular obtained for resins with a high coke content. The coke content is defined as the mass of residue that is obtained when a sample of an organic polymer is decomposed by pyrolysis, at a temperature of 900° C. under an inert atmosphere (nitrogen or argon), relative to the initial mass of this sample. The most beneficial resins have a coke content of greater than 50%.

Phenolic resins generally have such a coke content and are obtained by polycondensation of petrochemistry-based monomers: phenol and formaldehyde, which explains why they are also known as phenol-formaldehyde resins or formophenolic resins. The precursors of phenolic resins, phenol and formaldehyde, are, respectively, CMR 2 and 1B. These two compounds are thus monitored under Regulation (EC) No. 1907/2006 of the European Parliament (REACH) which is directed towards better protecting human health and the environment against the risks associated with chemical substances. It furthermore turns out that the polycondensation of phenol and formaldehyde is never complete, which accounts for the presence of volatile compounds and of water molecules that are very difficult to remove if a well-defined thermal cycle is not followed during this polycondensation and which may lead to materials that are porous in their native state and also to degassing events during the lifetime of the materials manufactured from phenolic resins. Now, this degassing events may have very harmful consequences in certain applications, for instance aerospace applications.

Given the current importance of phenolic resins in the plastics industry and the drawbacks thereof, novel thermosetting resins with properties similar to those of phenolic resins were obtained from different precursors. Thus, patent application WO 2017/129 661 describes such resins and processes for manufacturing same. Such resins have a coke content of greater than 50% and may thus be used as ablative materials. The precursors used are in particular aromatic molecules bearing propargyl ether functions. However, the excessive amount of energy released during their polymerization could lead to a thermal runaway during the manufacture of composite materials. Thus, in order to obtain an enthalpy of polymerization of about 800-900 J/g with a loss of mass that is as low as possible during the polymerization, it is necessary in the process described in said application to maintain a lengthy thermal treatment throughout the polymerization in order to prevent any thermal runaway. This solution is thus not optimized with respect to the manufacture of thick parts which may be up to several tens of millimetres thick.

The inventors realised that it was possible to reduce the energy released during the polymerization of resins bearing propargyl ether end groups by a factor of 6 by conversion of the propargyl ether function into a chromene function by means of homogeneous gold catalysis and thus to lower the enthalpy of polymerization to a value <500 J/g.

The article by Rajeev S. Menon et al. (J. Org. Chem. 2009, 74, pages 8901-8903) describes a process for converting the propargyl ether function into a chromene function by means of homogeneous gold catalysis using the catalyst (acetonitrile)[(2-biphenyl)di-tert-butylphosphine]gold(I) hexafluoroantimonate of certain aromatic compounds bearing propargyl ether functions such as propargylated catechol. However, this process has not been applied to propargylated resorcinol, to propargylated eugenol, to propargylated coupled eugenol, to propargylated coupled isoeugenol or to propargylated isoeugenol.

The present invention thus relates to a process for manufacturing chromenes which are intended for the preparation of thermosetting resins, comprising the step of transforming an aromatic propargyl ether of general formula (I) below

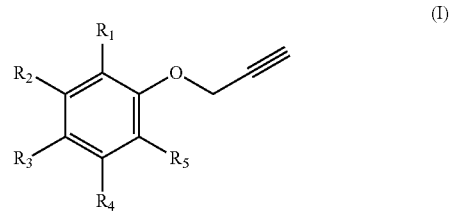

in which:
R$_1$ and R$_5$ represent, independently of each other, a hydrogen atom, a C$_2$-C$_6$ alkene, C$_2$-C$_6$ alkyne, O—(C$_1$-C$_6$)alkyl, O—(C$_2$-C$_6$)alkene or O—(C$_2$-C$_6$)alkyne group, on condition that at least one from among R$_1$ and R$_5$ represents a hydrogen atom and that the groups R$_1$ and R$_5$ do not represent an O-propargyl group;
R$_2$ and R$_4$ represent, independently of each other, a hydrogen atom, a C$_2$-C$_6$ alkene, C$_2$-C$_6$ alkyne such as propargyl, O—(C$_1$-C$_6$)alkyl, O—(C$_2$-C$_6$)alkene or O—(C$_2$-C$_6$)alkyne such as an O-propargyl;

and $R_3$ represents a hydrogen atom or a $C_2$-$C_6$ alkene group, the alkene group being optionally substituted with a group of general formula (II) below

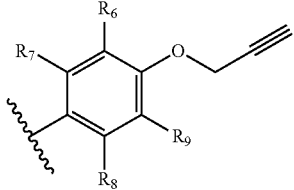

(II)

in which:
$R_6$ and $R_9$ represent, independently of each other, a hydrogen atom, a $C_2$-$C_6$ alkene, $C_2$-$C_6$ alkyne, O—($C_1$-$C_6$)alkyl, O—($C_2$-$C_6$)alkene or O—($C_2$-$C_6$)alkyne group, on condition that at least one from among $R_6$ and $R_9$ represents a hydrogen atom;
and $R_7$ and $R_8$ represent, independently of each other, a hydrogen atom, a $C_2$-$C_6$ alkene, $C_2$-$C_6$ alkyne such as propargyl, O—($C_1$-$C_6$)alkyl, O—($C_2$-$C_6$)alkene or O—($C_2$-$C_6$)alkyne such as an O-propargyl;
on condition that at least one from among $R_1$, $R_2$, $R_3$, $R_4$ and $R_5$ does not represent a hydrogen atom or a O—($C_1$-$C_6$)alkyl group;
and the cis/trans isomers thereof and the optical isomers thereof and the racemic mixtures thereof
into a chromene by homogeneous gold(I) catalysis with the catalyst (acetonitrile)[(2-biphenyl)di-tert-butylphosphine]gold(I) hexafluoroantimonate in an organic solvent under an inert or non-inert atmosphere.

For the purposes of the present invention, the term "$C_2$-$C_6$ alkene group" means any linear or branched alkene group of 2 to 6 carbon atoms, in particular the vinyl group, the allyl group or the 2-butenyl group.

For the purposes of the present invention, the term "$C_2$-$C_6$ alkyne group" means any linear or branched alkyne group of 2 to 6 carbon atoms, in particular the ethynyl group or the propargyl group.

For the purposes of the present invention, the term "O—($C_1$-$C_6$)alkyl group" means any linear or branched O-alkyl group of 1 to 6 carbon atoms, in particular the methoxy or ethoxy group.

For the purposes of the present invention, the term "O—($C_2$-$C_6$)alkene group" means any linear or branched O-alkene group of 2 to 6 carbon atoms.

For the purposes of the present invention, the term "O—($C_2$-$C_6$)alkyne group" means any linear or branched O-alkyne group of 2 to 6 carbon atoms, in particular the O-propargyl group.

Beneficially, the aromatic propargyl ether of general formula (I) is chosen from the group consisting of propargylated resorcinol, propargylated eugenol, propargylated coupled eugenol, propargylated coupled isoeugenol, propargylated isoeugenol and mixtures thereof and the cis/trans isomers thereof and the optical isomers thereof and the racemic mixtures thereof; more beneficially, it is propargylated resorcinol. These products are well known to those skilled in the art and may be prepared via well-known processes, such as those described in patent application WO 2017/129661. They have the benefit of being able to be obtained from compounds that can be biosourced such as resorcinol, eugenol, coupled eugenol, isoeugenol and coupled isoeugenol.

Propargylated resorcinol thus has the following general formula:

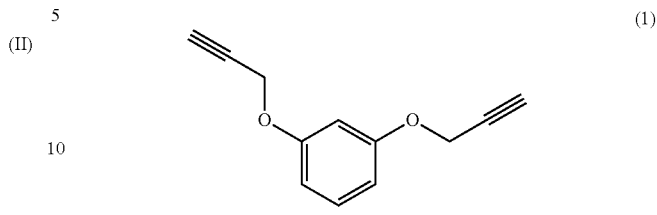

(1)

Propargylated eugenol thus has the following general formula:

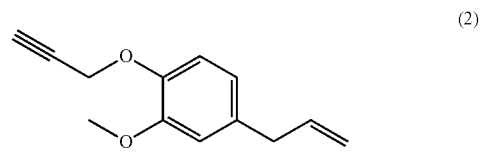

(2)

Propargylated coupled eugenol thus has the following general formula:

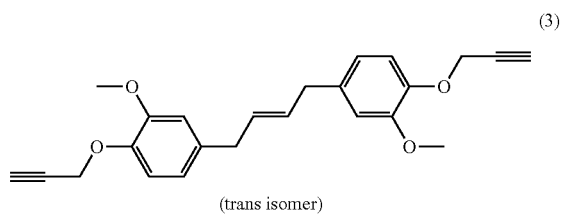

(3)

(trans isomer)

or the following general formula

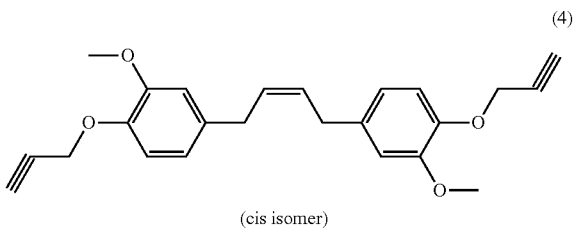

(4)

(cis isomer)

or a mixture of these two isomers.

Propargylated isoeugenol thus has the following general formula:

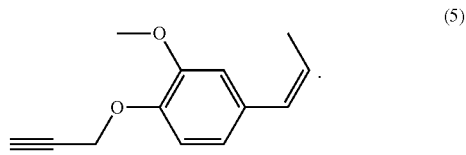

(5)

Propargylated coupled isoeugenol thus has the following general formula:

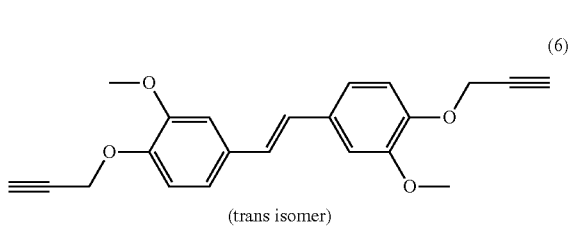

(trans isomer)

or the following general formula

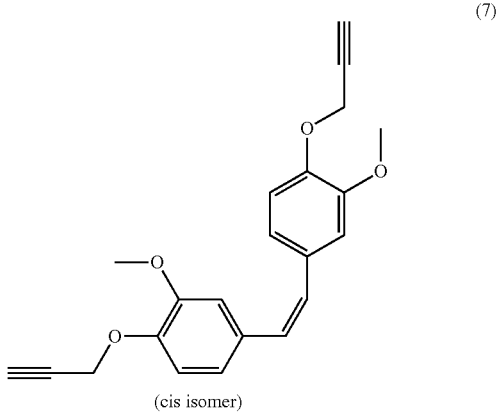

(cis isomer)

or a mixture of these two isomers.

The solvent used in the process according to the invention is an organic solvent. It may thus be dichloromethane, tetrahydrofuran, 2-methyltetrahydrofuran or mixtures thereof. Beneficially, it is a non-chlorinated solvent such as tetrahydrofuran, 2-methyltetrahydrofuran or mixtures thereof. Thus, in particular, the polar solvent is chosen from tetrahydrofuran and 2-methyltetrahydrofuran.

The catalyst for the process according to the present invention is thus (acetonitrile)[(2-biphenyl)di-tert-butylphosphine]gold(I) hexafluoroantimonate of general formula 8 below:

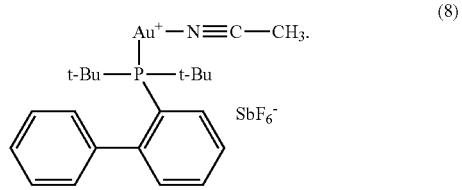

Beneficially, the content of catalyst in the reaction medium is between 0.01 mol % and 2 mol %, beneficially between 0.1 mol % and 0.5 mol %.

The catalyst must be removed at the end of the process. The process thus comprises a step of removing the catalyst from the reaction medium, beneficially via processes that are well known to those skilled in the art.

For example, in the case where the solvent is dichloromethane, this removal step may consist of simple filtration through a bed of silica. In the case where the solvent is a non-chlorinated solvent such as tetrahydrofuran or 2-methyltetrahydrofuran, this step is more difficult to perform. However, it is possible in this case to use a chromatography column with a petroleum ether/ethyl acetate eluent in particular in a 9/1 volume proportion, after evaporation of the solvent. Thus, beneficially, the process according to the present invention comprises an additional step of removing the solvent, in particular by evaporation, before the step of removing the catalyst. This solvent removal step may also take place after the removal of the catalyst.

Beneficially, the process according to the present invention is performed at a temperature of between 0 and 50° C., in particular between 20 and 50° C.

The process according to the invention may take place under an inert atmosphere (for example nitrogen or argon) or a non-inert atmosphere.

The reaction time depends on the reaction conditions such as the aromatic propargyl ethers used, the reaction temperature, the catalyst content and the polar solvent used, and may thus range from a few seconds (for example 30 s) to several hours (for example 5 hours).

The inventors realised that it was not necessary to have quantitative conversion of the propargyl ether functions into chromene in order to obtain a enthalpy of polymerization of less than 500 J/g. Specifically, the energy released during the polymerization for a given substrate is dependent on its molar mass and on its functionality. By using the energy released per propargyl function and per chromene function, combined with the molar mass of each substrate, it is possible theoretically to determine the maximum percentage of residual propargyl functions in order to be below 500 J/g. These values were compared with the experimental values obtained and are similar. Thus, Table 1 below indicates the theoretical percentage of residual propargyl functions in order to be below the 500 J/g of enthalpy of reaction during the polymerization. The theoretical percentage of residual propargyl functions is calculated in the following manner: (number of moles of propargyl functions at the end of the reaction)/(number of moles of propargyl functions before the start of the reaction)×100.

TABLE 1

| Substrate | M (g/mol) | Propargyl group functionality | Theoretical molar percentage of residual propargyl functions to achieve an enthalpy of 500 J/g |
|---|---|---|---|
| Propargylated resorcinol | 186.21 | 2 | 11 |
| Propargylated coupled eugenol | 376.44 | 2 | 39 |
| Propargylated coupled isoeugenol | 348.39 | 2 | 35 |

Thus, beneficially, the conversion of the aromatic propargyl ethers into chromene by the process according to the present invention is not total and the chromene obtained comprises residual propargyl functions. Beneficially, the molar percentage of residual propargyl functions in the chromene is less than 11% when the aromatic propargyl ether of general formula (I) is propargylated resorcinol, the molar percentage of residual propargyl functions in the chromene is less than 39% when the aromatic propargyl ether of general formula (I) is propargylated coupled eugenol and the molar percentage of residual propargyl functions in the chromene is less than 35% when the aromatic propargyl ether of general formula (I) is propargylated coupled isoeugenol.

In the case where the aromatic propargyl ether of general formula (I) is propargylated resorcinol, the chromene obtained by means of the process according to the invention may have the formula C and/or D below; beneficially, it is a mixture of formulae C and D.

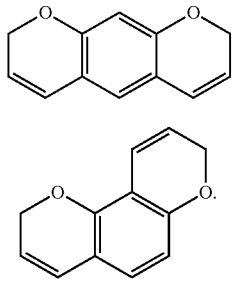

In particular, the molar proportion of chromene of formula C in the mixture is between 50% and 55% and that of chromene in formula D between 45% and 50%, depending on the polar solvent used. Thus, in the case where dichloromethane or 2-methyltetrahydrofuran is used, the mixture will comprise 55% of chromene of formula C and 45% of chromene of formula D and in the case where tetrahydrofuran is used, the mixture will comprise 50% of chromene of formula C and 50% of chromene of formula D.

In the case where the aromatic propargyl ether of general formula (I) is propargylated resorcinol, the chromene obtained by means of the process according to the invention may also have the formula A and/or B below:

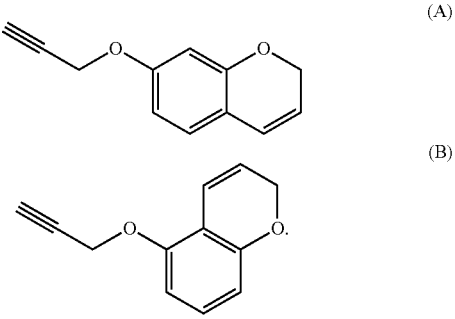

However, these molecules are generally rapidly converted into compounds of formulae C and D.

The process according to the present invention may also entail the formation of a coproduct such as 2-methylbenzofuran (impurity), in particular in a molar proportion relative to the total amount of species present in the reaction medium, of between 0.5% and 25%, in particular in the case where the aromatic propargyl ether of general formula (I) is propargylated resorcinol, in a molar proportion of between 0.5% and 10%. In a beneficial embodiment, the process according to the present invention comprises an additional step of purifying the reaction medium so as to remove this impurity, beneficially after the optional step of removing the catalyst and after the optional step of removing the solvent.

Beneficially, the molar yield of the reaction for the conversion of the aromatic propargyl ether into chromene is between 10% and 99%, more beneficially between 50% and 99% and even more beneficially between 60% and 99%.

The present invention also relates to a process for preparing a material made of thermoset resin, comprising the following successive steps:

a) implementation of the process according to the present invention, beneficially as described above;
b) polymerization of the reaction product obtained in step a) so as to obtain the material made of thermoset resin I;
c) recovery of the material made of thermoset resin obtained in step b).

In accordance with the invention, the polymerization of the resin may be performed via any means that is capable of inducing the polymerization/crosslinking of the chromene, and notably by applying a heat treatment or a light treatment (visible, UV or IR light).

In particular, step b) is performed by heat treatment, beneficially at a temperature of between 80° C. and 180° C., more beneficially by means of several stationary heating stages (in particular 3 or 4 or 5), without addition of other components, for instance 2 hours at 80° C., 2 hours at 100° C., 2 hours at 120° C., 2 hours at 140° C. and 2 hours at 180° C. or 1 hour at 80° C., 1 hour at 100° C., 1 hour at 120° C., 1 hour at 140° C., 1 hour at 160° C., 1 hour at 180° C., 1 hour at 200° C. or else 1 hour at 100° C., 1 hour 30 minutes at 150° C., 3 hours 30 minutes at 210° C. and 1 hour at 200° C. or even 1 hour at 80° C., 2 hours at 150° C. and 2 hours at 220° C.

More particularly, the process according to the invention may comprise between steps b) and c) an annealing step b1) at a temperature above 200° C. but below the degradation temperature of the resin, for example at 220° C. This step enables the thermomechanical properties of the resin to be improved.

In a beneficial embodiment, the material made of thermoset resin is a material forming the matrix of a composite material of the type comprising a matrix in which a reinforcement is present.

The reinforcement present in the composite material may be of various types. Thus, it may notably be a reinforcement consisting of fibres such as glass fibres, quartz fibres, carbon fibres, graphite fibres, silica fibres, metal fibres such as steel fibres or aluminium fibres, boron fibres, ceramic fibres such as silicon carbide fibres or boron carbide fibres, synthetic organic fibres such as aramid fibres, polyethylene fibres, polyester fibres or poly(p-phenylene benzobisoxazole) fibres, more commonly known by the abbreviation PBO, natural organic fibres such as hemp fibres, flax fibres or silk fibres, or alternatively mixtures of such fibres, in which case this reinforcement may be, depending on the nature of the fibres of which it is constituted, in the form of chopped yarns, of ground fibres, of continuous filament mats, of chopped filament mats, of stratifils (or "rovings"), of fabrics, of knitted fabrics, of felts, etc., or else in the form of complexes made by combination of various types of flat materials.

It may also be a reinforcement consisting of particles such as cork particles or refractory fillers such as tungsten, magnesium oxide, calcium oxide, alumina, silica, zirconium dioxide, titanium dioxide, beryllium oxide, etc.

Moreover, the manufacture of the composite material, and thus the addition of reinforcement to the resin, may be performed by any technique known to a person skilled in the art of composite materials, for instance by impregnation, by simultaneous injection-moulding, by autoclave drape moulding, by vacuum moulding, by moulding by low-pressure injection of resin (or "resin transfer moulding", RTM), by low-pressure "wet-route" cold-press moulding, by compound injection moulding (or "bulk moulding compound", BMC), by moulding by compression of preimpregnated mats (or "sheet moulding compound", SMC), by filament winding, by centrifugation or by pultrusion, impregnation being preferred in the case where the reinforcement consists of fibres.

Beneficially, the composite material is an ablative composite material and, more specifically, a thermal-protection ablative composite material, notably for the aerospace industry.

Beneficially, the enthalpy of polymerization of step b) is less than 500 J/g.

Beneficially, the coke content of the thermoset resin obtained in step c) is greater than 50%.

The present invention will be understood more clearly on reading the description of the examples that follow, which are given as non-limiting guides.

EXAMPLE 1

Conversion of Propargylated Resorcinol and Preparation of the Resin According to the Invention Synthesis of Propargylated Resorcinol 10 g (0.091 mol) of resorcinol (Alfa Aesar) are dissolved in 50 mL of dimethyl sulfoxide (DMSO), 50 g (0.363 mol) of potassium carbonate ($K_2CO_3$) are ground and then added with magnetic stirring, and the mixture is heated to 70° C. (ext). 14.45 mL (2.2 eq.) of propargyl chloride (ABCR) are added dropwise. The reaction is monitored by TLC with a 7/3 (volume) petroleum ether/diethyl ether eluent. After filtration and dilution in 100 mL of ethyl acetate, the medium is extracted with 3×100 mL of brine. The organic phase is dried over $MgSO_4$, filtered and concentrated under reduced pressure. The compound is purified by vacuum distillation (T° C.=120° C., 4.5 Pa). The yield is 77.4%.

Conversion of Propargylated Resorcinol

Weigh out 0.0415 g (1 mol %) of catalyst (acetonitrile)[(2-biphenyl)di-tert-butylphosphine]gold(I) hexafluoroantimonate (ABCR) in a pill bottle without any air exclusion precautions. 1 g (0.0054 mol) of propargylated resorcinol obtained previously is introduced into a Schlenk tube and then sealed. The medium is placed under inert atmosphere by successive emptying/filling with argon, at least three times. 50 mL of dry dichloromethane (DCM) (purified with a PureSolv MD7 device) are added by syringe. The catalyst is introduced against an argon counter-current using the pill bottle, and the medium is then conserved under argon. The reaction is monitored by TLC with a 9/1 (volume) petroleum ether/ethyl acetate eluent. After completion of the reaction (time: less than 1 minute), the medium is filtered through a thin bed of silica to remove the catalyst. The proportion of residual propargyl ether functions is estimated by $^1$H NMR at 0%. The yield is 65.8%. The molar proportion of chromene of formula C in the mixture is 50%. The molar proportion of chromene of formula D in the mixture is 50%. 6% of the compound 2-methylbenzofuran are present in the product. The product was not purified further, and is used in crude form. The proportion of residual propargyl ether functions of less than 11% complies with the set specifications.

Polymerization of the Chromene Obtained from Propargylated Resorcinol

The polymerization of the propargyl-chromene mixtures is performed by gradual raising of the temperature. In the case of a propargyl resorcinol-chromene mixture with a proportion of residual propargyl functions of less than 11% as obtained previously, the heat treatment applied is as follows: 2 hours at 80° C., 2 hours at 100° C., 2 hours at 110° C., 2 hours at 120° C., 2 hours at 130° C. and 2 hours at 150° C.

Annealing at 220° C. may be performed to increase the thermomechanical properties.

The coke content obtained before annealing is 63%.

EXAMPLE 2

Conversion of Propargylated Resorcinol

Weigh out 0.0207 g (0.5 mol %) of catalyst (acetonitrile)[(2-biphenyl)di-tert-butylphosphine]gold(I) hexafluoroantimonate (ABCR) in a pill bottle without any air exclusion precautions. 1 g (0.0054 mol) of propargylated resorcinol obtained according to the process indicated in Example 1 is introduced into a Schlenk tube. 50 mL of dichloromethane (DCM) are added without taking any air exclusion precautions. The catalyst is introduced using the pill bottle without taking any air exclusion precautions. The reaction is monitored by TLC with a 9/1 (volume) petroleum ether/ethyl acetate eluent. After completion of the reaction, the medium is filtered through a thin bed of silica to remove the catalyst. The proportion of residual propargyl ether functions is estimated by $^1$H NMR at 8%. The yield is 74%. 4.7% of the compound 2-methylbenzofuran are present in the product. The product was not purified further, and is used in crude form. The proportion of residual propargyl ether functions of less than 11% complies with the set specifications.

EXAMPLE 3

Conversion of Propargylated Resorcinol

Weigh out 0.0124 g (0.3 mol %) of catalyst (acetonitrile)[(2-biphenyl)di-tert-butylphosphine]gold(I) hexafluoroantimonate (ABCR) in a pill bottle without any air exclusion precautions. 1 g (0.0054 mol) of propargylated resorcinol obtained according to the process indicated in Example 1 is introduced into a Schlenk tube and then closed. The medium is placed under inert atmosphere by successive emptying/filling with argon, at least three times. 10 mL of dry tetrahydrofuran (THF) (purified with a PureSolv MD7 device) are added by syringe. The catalyst is introduced against an argon counter-current using the pill bottle, and the medium is then conserved under argon. The reaction is monitored by TLC with a 9/1 (volume) petroleum ether/ethyl acetate eluent. After completion of the reaction, the medium is filtered through a thin bed of silica to remove the catalyst. However, this catalyst is not retained. The proportion of residual propargyl ether functions is estimated by $^1$H NMR at 0%. The yield is 99.9%. The molar proportion of chromene of formula C in the mixture is 50%. The molar proportion of chromene of formula D in the mixture is 50%. 1.9% of the compound 2-methylbenzofuran are present in the product. The product was not purified further, and is used in crude form. The proportion of residual propargyl ether functions of less than 11% complies with the set specifications.

EXAMPLE 4

Conversion of Propargylated Resorcinol

Weigh out 0.0124 g (0.3 mol %) of catalyst (acetonitrile)[(2-biphenyl)di-tert-butylphosphine]gold(I) hexafluoroantimonate (ABCR) in a pill bottle without any air exclusion precautions. 1 g (0.0054 mol) of propargylated resorcinol obtained according to the process indicated in Example 1 is introduced into a Schlenk tube and then closed. The medium is placed under inert atmosphere by successive emptying/filling with argon, at least three times. 10 mL of methyltetrahydrofuran (Me-THF) are added by syringe. The catalyst is introduced against an argon counter-current using the pill bottle, and the medium is then conserved under argon. The reaction is monitored by TLC with a 9/1 (volume) petroleum ether/ethyl acetate eluent. After completion of the reaction, the medium is filtered through a thin bed of silica to remove the catalyst. However, this catalyst is not retained. The proportion of residual propargyl ether functions is estimated by $^1$H NMR at 1.5%. The yield is 86%. The molar proportion of chromene of formula C in the mixture is 55%. The molar proportion of chromene of formula D in the mixture is 45%. 7.1% of the compound 2-methylbenzofuran are present in the product. The product was not purified further, and is used in crude form. The proportion of residual propargyl ether functions of less than 11% complies with the set specifications.

EXAMPLE 5

Conversion of Propargylated Resorcinol

Weigh out 0.1244 g (0.3 mol %) of catalyst (acetonitrile)[(2-biphenyl)di-tert-butylphosphine]gold(I) hexafluoroantimonate (ABCR) in a pill bottle without any air exclusion precautions. 10 g (0.054 mol) of propargylated resorcinol obtained according to the process indicated in Example 1 are introduced into a Schlenk tube and then closed. The medium is placed under inert atmosphere by successive emptying/filling with argon, at least three times. 100 mL of dry tetrahydrofuran (THF) (purified with a PureSolv MD7 device) are added by syringe. The catalyst is introduced against an argon counter-current using the pill bottle, and the medium is then conserved under argon and heated to 50° C. The reaction is monitored by TLC with a 9/1 (volume) petroleum ether/ethyl acetate eluent. After reaction for 4 hours 30 minutes, the medium is filtered through a thin bed of silica to remove the catalyst. However, this catalyst is not retained. The proportion of residual propargyl ether functions is estimated by $^1$H NMR at less than 1%. The yield is greater than 97%. The molar proportion of chromene of formula C in the mixture is 50%. The molar proportion of chromene of formula D in the mixture is 50%. 3.3% of the compound 2-methylbenzofuran are present in the product. The product was not purified further, and is used in crude form. The proportion of residual propargyl ether functions of less than 11% complies with the set specifications.

EXAMPLE 6

Conversion of Propargylated Eugenol and Preparation of the Resin According to the Invention Synthesis of Propargylated Eugenol
Eugenol (Sigma-Aldrich) (200 g), K$_2$CO$_3$ (211 g) and dimethylformamide (DMF) (2000 mL) are placed in a 6 L round-bottomed flask and heated to 75° C. with mechanical stirring. Propargyl chloride (ABCR) at 70% in toluene (158.5 mL) is added dropwise via a dropping funnel, and the reaction medium is heated and stirred at 75° C. overnight. The reaction is monitored by TLC, eluting with 7/3 (volume) petroleum ether/diethyl ether. After the reaction, the reaction medium is filtered and then diluted and rinsed with ethyl acetate. The organic phase is rinsed with water until the aqueous phase has decolourized (four times). The organic phase is dried over MgSO$_4$ and concentrated under vacuum. The yield of crude product is 93%. The compound is purified by vacuum distillation (p=4.5 Pa and T° C.=60° C.). The yield of the distilled compound is 90%.
Conversion of Propargylated Eugenol
Weigh out 0.076 g (0.1 mol %) of catalyst (acetonitrile)[(2-biphenyl)di-tert-butylphosphine]gold(I) hexafluoroantimonate (ABCR) in a pill bottle without any air exclusion precautions. 20 g (0.0054 mol) of propargylated eugenol obtained previously are introduced into a 250 mL three-necked round-bottomed flask and then sealed. The medium is placed under an inert atmosphere with a gentle stream of argon. 100 mL of dry dichloromethane (purified with a PureSolv MD7 device) are added by syringe. The catalyst is introduced against an argon counter-current using the pill bottle, and the medium is then conserved under argon and placed in an oil bath preheated to 40° C. The reaction is monitored by TLC with a 9/1 (volume) petroleum ether/ethyl acetate eluent. After reaction for 1 hour, the medium is filtered through a thin bed of silica to remove the catalyst. The proportion of residual propargyl ether functions is estimated by $^1$H NMR at less than 1%. The yield is greater than 95%. 11% of the compound 2-methylbenzofuran are present in the product. The eugenol chromene is isolated by column chromatography with a 9/1 (volume) petroleum ether/ethyl acetate eluent. The yield of the pure product is 65%.
Polymerization of the Chromene Obtained from Propargylated Coupled Eugenol
The process performed is identical to that described in Example 1 for propargylated resorcinol, except for the fact that the heat treatment applied is as follows: 1 hour at 100° C., 1 hour 30 minutes at 150° C., 3 hours 30 minutes at 210° C. and 1 hour at 200° C.

EXAMPLE 7

Conversion of Propargylated Coupled Eugenol and Preparation of the Resin According to the Invention Synthesis of the Coupled Eugenol
26.675 g (0.1625 mol) of eugenol (Sigma-Aldrich) are placed in a 50 mL three-necked round-bottomed flask with a magnetic stirrer. 0.1337 g (0.1 mol %) of first-generation Grubbs catalyst (Sigma-Aldrich) is introduced using a pill bottle against a counter-current of argon. The medium is directly placed under high vacuum (3 kPa) and left stirring for 12 hours. A $^1$H NMR spectrum of the crude product is taken to determine the conversion of the eugenol. The conversion is 67 mol % of coupled eugenol compound, the remaining 37 mol % being a mixture of unreacted eugenol and of its isomer, isoeugenol. The stoichiometric proportion is evaluated by 1H NMR at 34.3%/65.7% for the cis- and trans-coupled eugenol compounds, respectively. The medium is dissolved in a minimum amount of refluxing ether and then left to stand at room temperature. The solid is filtered off under reduced pressure on a No. 4 porosity sinter, and then washed with 4×20 mL of cyclohexane. The solid is dried under high vacuum using a vane pump, for 10 hours. In order to remove the first-generation Grubbs catalyst, the solid is dissolved in dichloromethane (DCM) and then filtered through Celite. A black deposit is observed on the Celite. The organic phase is dried under reduced pressure. The yield obtained is 25%.

Synthesis of Propargylated Coupled Eugenol 3 g (0.010 mol) of coupled eugenol obtained previously are dissolved in 30 mL (10 eq.) of DMF. 5.52 g (4 eq.) of finely ground potassium carbonate ($K_2CO_3$) are added with magnetic stirring. 2.78 mL (2.5 eq.) of propargyl bromide (Alfa Aesar) (80 mol % in toluene) are added via a dropping funnel. Magnetic stirring is continued for 12 hours. Completion of the reaction is monitored by TLC, eluting with 50/50 (volume) petroleum ether/ethyl acetate. After filtering off the $K_2CO_3$ and washing with DMF, an excess of distilled water (200 mL) is added to precipitate the product. The solid is recovered. 200 mL of ethyl acetate are added to the medium for the extraction. The aqueous phase is discarded. The solid recovered previously is redissolved in the organic phase. The organic phase is washed three times with distilled water (3×100 mL) and once with brine (1×100 mL). The organic phase is dried over $MgSO_4$, filtered and concentrated under reduced pressure. The yield is 90%.

Conversion of Propargylated Coupled Eugenol

Weigh out 0.0308 g (1 mol %) of catalyst (acetonitrile)[(2-biphenyl)di-tert-butylphosphine]gold(I) hexafluoroantimonate (ABCR) in a pill bottle without any air exclusion precautions. Introduce 1.5 g (0.0040 mol) of propargylated coupled eugenol obtained previously into a 100 mL Schlenk tube and perform three vacuum/argon cycles. Next, add 10 mL of dry dichloromethane (purified with a PureSolv MD7 device) by syringe. Introduce the catalyst against a countercurrent of argon and then seal the medium under argon. The reaction is monitored by TLC with a 9/1 (volume) petroleum ether/ethyl acetate eluent. After reaction for 5 minutes, the medium is filtered through a No. 4 porosity sinter with a short bed of silica, using DCM. The DCM is evaporated off under reduced pressure on a rotary evaporator. The conversion is 100%. The proportion of residual propargyl ether functions is estimated by $^1$H NMR at 0%. The yield of crude product is 77.6%. The crude reaction product is composed of 15% of the compound 2-methylbenzofuran. The product is purified by column chromatography with a 9/1 (volume) petroleum ether/ethyl acetate eluent. The pure coupled eugenol chromene is obtained in a yield of 40%. The proportion of residual propargyl ether functions of less than 39% complies with the set specifications.

Polymerization of the Chromene Obtained from Propargylated Coupled Eugenol

The process performed is identical to that described in Example 1 for propargylated resorcinol, except for the fact that the heat treatment applied is as follows: 1 hour at 80° C., 2 hours at 150° C., 2 hours at 220° C. The coke content obtained before annealing is 56%.

EXAMPLE 8

Conversion of Propargylated Coupled Isoeugenol and Preparation of the Resin According to the Invention Synthesis of the Coupled Isoeugenol 0.0181 g (0.017%) of Grubs II catalyst (Umicore M2a) is placed in a 50 mL round-bottomed flask with a magnetic stirrer, and 20 g (0.122 mol) of isoeugenol (Sigma-Aldrich) are then added. The medium is placed under a stream of argon and heated at 90° C. The medium turns solid after 3 minutes of reaction. After cooling, a $^1$H NMR spectrum of the crude product is taken to determine the conversion of the isoeugenol to stilbene. The degree of conversion is 90%. Only the trans-compound is observed. The product is recovered by suspension in 4 volumes of DCM. The medium is refluxed for 1 hour until dissolution is complete, and is then left to stand at room temperature overnight. The suspension is filtered through a sinter and washed with 1 volume of cyclohexane. The isolated yield is 67%.

Synthesis of Propargylated Coupled Isoeugenol 10 g (0.037 mol) of eugenol stilbene obtained previously are dissolved in 100 mL (10 eq.) of DMF. 25 g (4.5 eq.) of finely ground potassium carbonate ($K_2CO_3$) are added with magnetic stirring. 10.23 mL (2.5 eq.) of propargyl bromide (Alfa Aesar) (80 mol % in toluene) are added by syringe. Magnetic stirring is continued for 12 hours. Completion of the reaction is monitored by TLC, eluting with 50/50 (volume) petroleum ether/ethyl acetate. The conversion is total after reaction overnight. The $K_2CO_3$ is filtered off and then washed with ethyl acetate. The compound is extracted with 2×100 mL of ethyl acetate. The organic phases are washed with 4×100 mL of brine. The organic phases are dried over $MgSO_4$, filtered and concentrated under reduced pressure. The yield of the product is 30%.

Conversion of the Propargylated Coupled Isoeugenol

Weigh out 0.0054 g (0.5 mol %) of catalyst (acetonitrile)[(2-biphenyl)di-tert-butylphosphine]gold(I) hexafluoroantimonate (ABCR) in a pill bottle without any air exclusion precautions. Introduce 0.4864 g (0.0014 mol) of propargylated eugenol stilbene obtained previously into a 100 mL Schlenk tube and perform three vacuum/argon cycles. Next, add 10 mL of dry DCM (purified with a PureSolv MD7 device) by syringe. Introduce the catalyst against a countercurrent of argon. Add a balloon filled with argon. The medium is heated to between 30 and 40° C. to fully dissolve the propargylated eugenol stilbene in the DCM. The reaction is monitored by TLC with a 5/5 (volume) petroleum ether/ethyl acetate eluent. After the reaction, the medium is filtered through a No. 4 porosity sinter with a short bed of silica, using DCM. The DCM is evaporated off under reduced pressure on a rotary evaporator. The proportion of residual propargyl ether functions is estimated by $^1$H NMR at less than 1%. The yield of crude product is 56%. The crude reaction product is composed of 14% of compound of the 2-methylbenzofuran type, estimated by $^1$H NMR. The product was not purified further, and is used in crude form. The proportion of residual propargyl ether functions of less than 35% complies with the set specifications.

Polymerization of the Chromene Obtained from Propargylated Coupled Isoeugenol

The process performed is identical to that described in Example 1.

The enthalpy of reaction is 170 J/g.

EXAMPLE 9

Conversion of Propargylated Isoeugenol and Preparation of the Resin According to the Invention Synthesis of Propargylated Isoeugenol 20 g (0.130 mol) of isoeugenol (Sigma-Aldrich) are dissolved in 100 mL (5 eq.) of DMF. 33.67 g (2 eq.) of finely ground potassium carbonate ($K_2CO_3$) are added with magnetic stirring. 20.35 mL (1.5 eq.) of propargyl bromide (Alfa Aesar) (80 mol % in toluene) are added via a dropping funnel. Magnetic stirring is continued for 12 hours. Completion of the reaction is monitored by TLC, eluting with 70/30 (volume) petroleum ether/ethyl acetate. After filtering off the $K_2CO_3$ and washing with ethyl acetate, 100 mL of ethyl acetate are added to the medium for the extraction. The organic phase is washed three times with distilled water (3×100 mL) and once with brine (1×100 mL). The organic phase is dried over MgSO$_4$, filtered and concentrated under reduced pressure. The yield is 91%.

The compound is purified by vacuum distillation in a Kugelrohr glass oven (p=15 Pa and heating T° C.=140° C.). The compound is recovered in the form of white crystals. The overall yield after purification is 73%.

Conversion of the Propargylated Isoeugenol

Weigh out 0.3818 g (0.0005 mol) of catalyst (acetonitrile)[(2-biphenyl)di-tert-butylphosphine]gold(I) hexafluoroantimonate (ABCR) in a pill bottle without any air exclusion precautions. Introduce 10 g (0.05 mol) of propargylated isoeugenol obtained previously into a 100 mL three-necked round-bottomed flask on which is mounted a condenser. The medium is placed under argon via one of the inlets of the three-necked flask. 40 mL of dry DCM (purified with a PureSolv MD7 device) are added by syringe. The catalyst is introduced against an argon counter-current using the pill bottle by the second inlet of the three-necked flask and the medium is conserved under argon. The reaction is monitored by TLC with a 9/1 (volume) petroleum ether/ethyl acetate eluent. After 5 minutes, the conversion is total: the proportion of the compound 2-methylbenzofuran is estimated by $^1$H NMR at 13.6%. The medium is concentrated under reduced pressure and then purified by column chromatography by solid deposition, with a 9/1 (volume) petroleum ether/ethyl acetate eluent. The yield of isoeugenol chromene is 69%.

It is possible to reduce the amount of 2-methylbenzofuran formed by performing the reaction at low temperature (0° C.). After 2 hours, the conversion is total: the proportion of the compound 2-methylbenzofuran is estimated by $^1$H NMR at 4.2%.

Polymerization of the Chromene Obtained from Propargylated Isoeugenol

The process performed is identical to that described in Example 1.

The invention claimed is:

1. A process for manufacturing chromenes which are intended for the preparation of thermosetting resins, comprising the step of transforming an aromatic propargyl ether of general formula (I) below

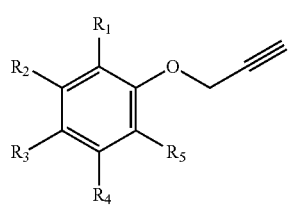

(I)

in which:
R$_1$ and R$_5$ represent, independently of each other, a hydrogen atom, a C$_2$-C$_6$ alkene, C$_2$-C$_6$ alkyne, O—(C$_1$-C$_6$)alkyl, O—(C$_2$-C$_6$)alkene or O—(C$_2$-C$_6$)alkyne group, on condition that at least one from among R$_1$ and R$_5$ represents a hydrogen atom and that the groups R$_1$ and R$_5$ do not represent an O-propargyl group;
R$_2$ and R$_4$ represent, independently of each other, a hydrogen atom, a C$_2$-C$_6$ alkene, C$_2$-C$_6$ alkyne, O—(C$_1$-C$_6$)alkyl, O—(C$_2$-C$_6$)alkene or O—(C$_2$-C$_6$)alkyne;
and R$_3$ represents a hydrogen atom or a C$_2$-C$_6$ alkene group, the alkene group being optionally substituted with a group of general formula (II) below

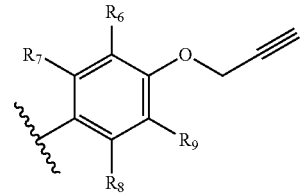

(II)

in which:
R$_6$ and R$_9$ represent, independently of each other, a hydrogen atom, a C$_2$-C$_6$ alkene, C$_2$-C$_6$ alkyne, O—(C$_1$-C$_6$)alkyl, O—(C$_2$-C$_6$)alkene or O—(C$_2$-C$_6$)alkyne group, on condition that at least one from among R$_6$ and R$_9$ represents a hydrogen atom;
and R$_7$ and R$_8$ represent, independently of each other, a hydrogen atom, a C$_2$-C$_6$ alkene, C$_2$-C$_6$ alkyne, O—(C$_1$-C$_6$)alkyl, O—(C$_2$-C$_6$)alkene or O—(C$_2$-C$_6$)alkyne;
on condition that at least one from among R$_1$, R$_2$, R$_3$, R$_1$ and R$_5$ does not represent a hydrogen atom or a O—(C$_1$-C$_6$)alkyl group;
and the cis/trans isomers thereof and the optical isomers thereof and the racemic mixtures thereof into a chromene by homogeneous gold(I) catalysis with the catalyst (acetonitrile)[(2-biphenyl)di-tert-butylphosphine]gold(I) hexafluoroantimonate in an organic solvent under an inert or non-inert atmosphere
wherein the aromatic propargyl ether of general formula (I) is chosen from the group consisting of propargylated resorcinol, propargylated eugenol, propargylated coupled eugenol, propargylated coupled isoeugenol, propargylated isoeugenol and mixtures thereof and the cis/trans isomers thereof and the optical isomers thereof and the racemic mixtures thereof.

2. The process according to claim 1, wherein the molar percentage of residual propargyl functions in the chromene is less than 11% when the aromatic propargyl ether of general formula (I) is propargylated resorcinol, the molar percentage of residual propargyl functions in the chromene is less than 39% when the aromatic propargyl ether of general formula (I) is propargylated coupled eugenol and the molar percentage of residual propargyl functions in the chromene is less than 35% when the aromatic propargyl ether of general formula (I) is propargylated coupled isoeugenol.

3. The process according to claim 1, wherein the organic solvent is chosen from tetrahydrofuran and 2-methyltetrahydrofuran.

4. The process according to claim 1, wherein the content of catalyst in the reaction medium is between 0.1 mol % and 2 mol %.

5. The process according to claim 4, wherein the content of catalyst in the reaction medium is between 0.1 mol % and 0.5 mol %.

6. The process according to claim 1, wherein the aromatic propargyl ether of general formula (I) is propargylated resorcinol and wherein the chromene obtained has the formula C and/or D below

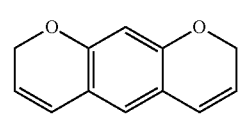

(C)

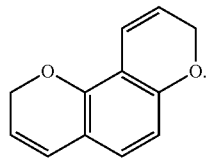
(D)

7. The process according to claim 1, wherein the catalyst is removed from the reaction medium at the end of the process.

8. A process for preparing a material made of thermoset resin, comprising the following successive steps:
   a) implementation of the process according to claim 1;
   b) polymerization of the reaction product obtained in step a) so as to obtain the material made of thermoset resin;
   c) recovery of the material made of thermoset resin obtained in step b).

9. The process according to claim 8, wherein the enthalpy of polymerization of step b) is less than 500 J/g.

10. The process according to claim 8, wherein the coke content of the thermoset resin obtained in step c) is greater than 50%.

11. The process according to claim 1, wherein the aromatic propargyl ether of general formula (I) is propargylated resorcinol.

12. The process according to claim 6, wherein the chromene obtained is a mixture of the formulae C and D.

* * * * *